United States Patent [19]

Gallegra et al.

[11] Patent Number: 5,171,879
[45] Date of Patent: Dec. 15, 1992

[54] PROCESS FOR THE PREPARATION OF CHLORINATED CARBOXYLIC ACID ESTERS

[75] Inventors: Pasquale Gallegra, Muttenz; Gerhard Degischer, Füllinsdorf, both of Switzerland

[73] Assignee: Säurefabrik Schweizerhall, Schweizerhalle, Switzerland

[21] Appl. No.: 849,572

[22] Filed: Mar. 10, 1992

[30] Foreign Application Priority Data

Mar. 11, 1991 [CH] Switzerland .................. 715/91

[51] Int. Cl.$^5$ ............................................. C07C 67/02
[52] U.S. Cl. ...................... 560/266; 560/21; 560/64; 560/56; 560/100; 560/111; 560/125; 560/126; 560/156; 560/179; 560/223
[58] Field of Search ............ 560/266, 21, 56, 64, 560/100, 111, 125, 126, 156, 179, 223

[56] References Cited

U.S. PATENT DOCUMENTS 3,697,507 10/1972 Frederiksen et al. .......... 260/239.1
3,850,908 11/1974 von Daehne et al. ........ 260/239.1

FOREIGN PATENT DOCUMENTS 0083484 7/1983 European Pat. Off. .
0406660 1/1991 European Pat. Off. .
1951012 4/1970 Fed. Rep. of Germany .
2269508 11/1975 France .
1313850 5/1987 U.S.S.R. .
2152504 8/1985 United Kingdom .

OTHER PUBLICATIONS

Grynkiewicz et al., Polish Journal of Chemistry, vol. 61 (1987) pp. 443–447.
Binderup et al., Synthetic Communications, vol. 14, No. 9 (1984) pp. 857–864.
Rasmussen et al., J. Amer. Chem. Soc., vol. 89, No. 21 (1967) pp. 5439–5445.
Wheeler et al., J. Med. Chem., vol. 22, No. 6 (1979) pp. 657–661.
Euranto et al., Acta. Chem. Scand., vol. 20 (1966) pp. 1273–1280.
Neuenschwander et al., Helv. Chim. Acta., vol. 60 (1977) pp. 1061–1072.
Ulich et al., J. Amer. Chem. Soc., vol. 43 (1921) pp. 660–667.
Kochhar et al., J. Org. Chem., vol. 48 (1983) pp. 1765–1767.
Olah et al., Synthesis, Nov. 1982, pp. 962–963.
Michie et al., Synthesis (1981), p. 824.

Primary Examiner—Paul J. Killos
Attorney, Agent, or Firm—Wenderoth, Lind & Ponack

[57] ABSTRACT

The invention relates to a novel process for the preparation of chlorinated carboxylic acid esters of formula I wherein $R_1$ is alkyl, alkenyl, alkynyl, cycloalkyl, aralkyl or aryl and $R_2$ hydrogen is alkyl or cycloalkyl, which process comprises reacting an acylal of formula II

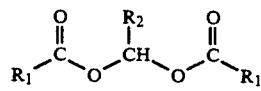

with thionyl chloride.

14 Claims, No Drawings

PROCESS FOR THE PREPARATION OF CHLORINATED CARBOXYLIC ACID ESTERS

The invention relates to a novel process for the preparation of chlorinated carboxylic acid esters of formula I

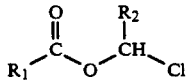

wherein $R_1$ is alkyl, alkenyl, alkynyl, cycloalkyl, aralkyl or aryl and $R_2$ hydrogen is alkyl or cycloalkyl, which process comprises reacting an acylal of formula II

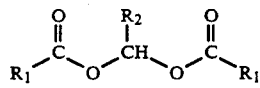

with thionyl chloride.

Alkyl is preferably lower alkyl, such as straight-chained or branched $C_1$–$C_7$alkyl, such as methyl, ethyl, propyl, isopropyl, butyl, isobutyl, sec-butyl, tert-butyl, pentyl, isopentyl, sec-pentyl, neopentyl or a hexyl or heptyl group, but it may also be a $C_8$–$C_{14}$alkyl group, such as an octyl, nonyl or decyl group. In the case of $R_1$ preference is given to methyl, ethyl and also secondary-linear and branched $C_3$–$C_7$alkyl groups, such as isopropyl, but-2-yl, pent-3-yl, tert-butyl or 2-methylbut-2-yl, and in the case of $R_2$ preference is given to linear $C_1$–$C_4$alkyl groups, such as methyl, ethyl, propyl or butyl.

Alkenyl is preferably straight-chained or branched $C_2$–$C_7$alkenyl, such as ethenyl, propenyl, for example allyl, isopropenyl, methallyl (crotyl), butenyl or 2-methylprop-2-enyl.

Alkynyl is, for example, $C_3$–$C_7$alkynyl, such as propargyl.

Cycloalkyl is, for example, 3- to 8-membered, such as 5- to 7-membered, cycloalkyl, for example cyclopropyl, cyclobutyl, cyclopentyl, cyclohexyl or cycloheptyl.

Aryl is, for example, phenyl or naphthyl; aralkyl is, for example, mono-, di- or tri-phenyl-$C_1$–$C_4$alkyl, such as benzyl, 1-phenylethyl, diphenylmethyl or triphenylmethyl. Phenyl and naphthyl and the phenyl moiety of mono-, di- or tri-phenyl-$C_1$–$C_4$alkyl may be unsubstituted or substituted, such as mono-, di- or tri-substituted, by customary substituents, such as lower alkyl, for example methyl, lower alkoxy, for example methoxy, halogen, for example chlorine or bromine, trifluoromethyl and/or nitro, but they are preferably unsubstituted.

Unless indicated otherwise, the expression "lower" used in the definition of radicals such as lower alkyl and lower alkoxy means that the radicals concerned contain up to and including 7, preferably up to and including 4, carbon atoms.

The compounds of formula I are valuable intermediates in organic synthesis, especially for the preparation of active ingredients for medicaments. They react with amines, alcohols and carboxylic acids with the introduction of the group of the formula

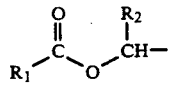

to form the corresponding substituted amines, ethers and esters. The compounds of formula I are suitable especially for the preparation of corresponding acyloxyalkyl esters of β-lactam antibiotics, such as penicillins, for example 6-[D-(—)-α-aminophenylacetamido]-penicillanic acid (pivaloyloxy)methyl ester hydrochloride (Pivampicillin), and of cephalosporins, for example 7-[(2-amino-4-thiazolyl)-(methoxyiminoacetylamino)-3-methyl-8-oxo]-5-thia-1-azabicyclo[4.2.0]octenecarboxylic acid (pivaloyloxy)methyl ester (Cefetamet pivoxil) and the like.

The invention relates especially to the preparation of compounds of formula I wherein $R_1$ is $C_1$–$C_{14}$alkyl, $C_2$–$C_7$alkenyl, $C_3$–$C_7$alkynyl, or 3- to 8-membered cycloalkyl; or is phenyl or naphthyl each of which is unsubstituted or substituted by $C_1$–$C_4$alkyl, $C_1$–$C_4$alkoxy, halogen, trifluoromethyl and/or by nitro, or mono-, di- or tri-phenyl-$C_1$–$C_4$alkyl that is unsubstituted or substituted in the phenyl moiety by $C_1$–$C_4$alkyl, $C_1$–$C_4$alkoxy, halogen, trifluoromethyl and/or by nitro, and $R_2$ hydrogen is $C_1$–$C_7$alkyl or 3- to 8-membered cycloalkyl.

The invention relates very especially to the preparation of compounds of formula I wherein $R_1$ is $C_1$–$C_7$alkyl, such as methyl or tert-butyl, and $R_2$ is hydrogen or $C_1$–$C_4$alkyl.

The invention relates preferably to the preparation of compounds of formula I wherein $R_1$ is methyl, ethyl or secondary-linear or branched $C_3$–$C_7$alkyl, such as isopropyl or tert-butyl, and $R_2$ is hydrogen or linear $C_1$–$C_4$alkyl, such as methyl or ethyl.

The invention relates most especially to the preparation of compounds of formula I wherein $R_1$ is methyl, ethyl or secondary-linear or branched $C_3$–$C_7$alkyl, such as isopropyl or tert-butyl, and $R_2$ is hydrogen.

The invention relates specifically to the preparation of the compounds of formula I mentioned in the Examples, especially of chloromethyl pivalate ($R_1$=tert-butyl, $R_2$=hydrogen).

The customary process for the preparation of compounds of formula I comprises condensing an acid chloride of formula IV

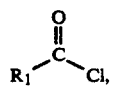

wherein $R_1$ is methyl or tert-butyl, with paraformaldehyde in the presence of zinc chloride, or reacting an approximately equimolar mixture of an appropriate aldehyde of formula V

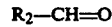

and an acid of formula VI

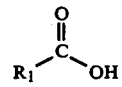

with an excess of thionyl chloride in the presence of zinc chloride. Both variants of this process have decided disadvantages. In particular, it is known that the product obtained according to the first variant is in all cases contaminated by approximately 10 mol-% of the corresponding bis(α-chloroalkyl)ether, and a considerably larger amount of that compound is formed according to the second variant, as is shown by the Comparison Example. However, owing to their toxicity, which especially in the case of the lower homologues of the group is very high, bis(α-chloroalkyl)ethers give rise to considerable toxicological safety problems. That undesired by-product can be separated off only with great difficulty and can be removed virtually completely only at great expense. Moreover, in addition to sulfur dioxide and hydrogen chloride, a large number of other by-products is always formed; according to the first variant, for example, acylal acetals of formula VII

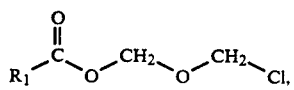  (VII)

anhydrides of formula VIII

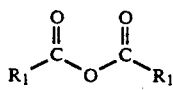  (VIII)

and acylals of formula II are formed, and according to the second process variant acid chlorides of formula IV are formed. These by-products, as well as excess aldehyde of formula V and the condensation agent used, make isolation of the desired product considerably more difficult.

For that reason, there has been no lack of attempts to develop processes for the preparation of compounds of formula I that avoid the mentioned disadvantages. However, the proposed solutions that have hitherto been disclosed are also toxicologically unacceptable, or are too expensive or too complex for industrial application.

For example, it has been proposed to react the acid of formula VI in the form of an alkali metal salt with an appropriate chlorosulfonic acid (α-chloro)alkyl ester of formula IX

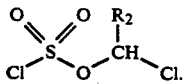  (IX)

However, reagents of formula IX are not very stable and, on account of their high toxicity, they in turn give rise to considerable toxicological safety problems, which prevent the use of this process on an industrial scale.

In accordance with another proposal, methylene diacetate or methylene dibenzoate (II; $R_1$=methyl or phenyl, $R_2$=hydrogen) is reacted with trimethylchlorosilane at 120° C. in the presence of the 0.2-fold molar amount of aluminium trichloride. However, the process is suitable to only a very limited extent for the preparation of compounds of formula I.

For example, in the reaction of methylene dibenzoate, chloromethyl benzoate was isolated in a yield of only about 50%. When methylene diacetate was used as starting material, the reaction mixture comprised about 40 mol-% chloromethyl acetate, as was determined by evaluation of the $^1$H-NMR spectrum, but that product could not be isolated. A further disadvantage is that mixtures of oligo- and poly-silanols are always formed in an equimolar amount as undesired by-products which are volatilized only with difficulty and which can be disposed of on a technical scale only at great expense. It is a common feature of the known alternative proposals that it is possible to use as chlorine donor only specially selected, either highly toxic chlorosulfonic acid (α-chloro)alkyl esters of formula IX or trimethylchlorosilane reagents that are difficult to handle on an industrial scale. In addition, in the second alternative proposal, only moderate yields are obtained owing to the drastic reaction conditions that are necessary.

The invention was therefore based on the hitherto unsolved problem of developing a process for the preparation of compounds of formula I that avoids the disadvantages of the known processes. This problem is solved very well by the process according to the invention.

The process according to the invention is based on the discoveries, which are surprising in the light of the prior art, that condensation agents, such as zinc chloride or aluminium trichloride, are completely unnecessary, that thionyl chloride can be used as the chlorine donor instead of special reagents that are highly toxic and/or difficult to handle, without the yield, reaction velocity and product purity being impaired, and that the formation of bis(α-chloroalkyl)ethers can be very largely avoided. For example, the Example of operation given below shows that approximately 100 times less bis(chloromethyl)ether is formed according to the invention than is the case with the already optimised known procedure according to the Comparison Example. A further advantage is that the reaction is very easily monitored, and fewer by-products are formed.

The reaction of compounds of formula II with thionyl chloride is generally carried out using at least an equimolar amount of thionyl chloride, in the presence or absence of solvents or diluents, advantageously at elevated temperature and with subsequent working up by distillation.

There come into consideration as solvents, for example, haloalkanes or haloaromatic compounds, such as di, tri- or tetra-chloro-$C_1$–$C_4$alkanes, for example methylene chloride, trichloroethane or chlorobenzene. Advantageously, however, the reaction according to the invention may be carried out without a solvent, in which case a slight excess over the molar amount of the compound of the formula II, for example from approximately 1.1 times to approximately twice, such as from approximately 1.25 to approximately 1.75 times, especially from 1.4 to 1.75 times the molar amount, of thionyl chloride is advantageously used.

The reaction temperature is not critical and may be from approximately 0° C. to approximately 150° C., preferably from 20° C. to 150° C. However, in order to achieve an adequate reaction velocity and optimum conversion within a period of from 2 to 12 hours, especially approximately from 4 to 8 hours, the reaction is advantageously carried out at elevated temperature, preferably in a temperature range of from 40° C. to 150° C., for example from approximately 40° C. to approximately 120° C., such as from approximately 60° C. to approximately 100° C., especially from approximately 70° C. to approximately 80° C.

The removal of excess thionyl chloride and acid chloride of formula IV formed as by-product from the reaction product by distillation is advantageously carried out under reduced pressure, for example at from approximately 1 mbar to approximately 50 mbar, especially at from approximately 10 mbar to approximately 30 mbar.

In a preferred form of the process according to the invention, an acylal of formula II is heated to approximately from 70° C. to 80° C., approximately 1.25 to approximately 1.75 times the molar amount of thionyl chloride is added, the mixture is allowed to react for approximately from 4 to 8 hours, and then distillation is carried out under reduced pressure, for example at from approximately 10 mbar to approximately 30 mbar.

The starting materials of formula II are known or are prepared according to processes known per se.

For example, the acylals (aldehyde acylates) of formula II can be prepared according to one of the processes mentioned in "Houben-Weyl - Methoden der organischen Chemie", E. Müller et al. (eds.), Vol. 7, Part 1, 4th edition, Georg Thieme Verlag, Stuttgart, p. 442, or according to Kochhar et al., J. Org. Chem. 48, 1765 (1983), Olah et al., Synthesis p. 962, (1982) or Michie et al., Synthesis p. 824, (1981).

The following Examples serve to illustrate the invention; temperatures are given in degrees Celsius, pressures in mbar.

EXAMPLE OF OPERATION 169.9 g of methylene dipivalate (II; $R_1$=tert-butyl, $R_2$=hydrogen) are heated to approximately 75°, and 160.0 g of thionyl chloride are added, with stirring. The mixture is then stirred at 75° for 5 hours. In the course of the reaction a total of 45.1 g of sulfur dioxide are freed. The composition of the reaction mixture is determined in an aliquot sample of the reaction mixture. The reaction balance, taking account of the volatile constituents collected separately, is as follows:

| | |
|---|---|
| 106.5 g | chloromethyl pivalate |
| 45.1 g | sulfur dioxide |
| 85.2 g | pivalic acid chloride |
| 75.8 g | thionyl chloride |
| 17.0 g | methylene dipivalate |
| 0.3 g | bis(chloromethyl)ether |

The reaction mixture is then hydrolysed by the addition of water and separated by distillation under reduced pressure (approximately 20 mbar); there is obtained at least 99% pure chloromethyl pivalate which comprises less than 0.1 ppm of the toxic bis(chloromethyl)ether, in a yield of 90% of the theoretical yield.

COMPARISON EXAMPLE 1.7 g of zinc chloride are stirred with 0.8 ml of water, and 180.0 g of thionyl chloride are added carefully, with stirring. The mixture is stirred for one hour at room temperature, and then a suspension of 42.1 g of paraformaldehyde in 85.0 g of molten pivalic acid is added in portions at 70°, with stirring. The mixture is heated at 100° for one hour, with stirring. In the course of the reaction a total of 36.5 g of hydrogen chloride and 80 g of sulfur dioxide are freed. The composition of the reaction mixture is determined in an aliquot sample. The reaction balance, taking account of the volatile constituents collected separately, is as follows:

| | |
|---|---|
| 106.5 g | chloromethyl pivalate |
| 80.0 g | sulfur dioxide |
| 13.0 g | pivalic acid chloride |
| 30.0 g | thionyl chloride |
| 52.0 g | bis(chloromethyl)ether |
| 36.5 g | hydrogen chloride |
| 1.7 g | zinc chloride |

The reaction mixture is separated by distillation under reduced pressure (approximately 20 mbar); there is obtained approximately 99% pure chloromethyl pivalate, in a yield of 85.2% of the theoretical yield.

What is claimed is:

1. A process for the preparation of chlorinated carboxylic acid esters of formula I

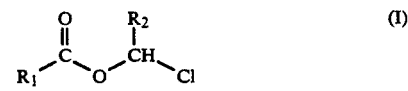

wherein $R_1$ is alkyl, alkenyl, alkynyl, cycloalkyl, aralkyl or aryl and $R_2$ hydrogen is alkyl or cycloalkyl, which process comprises reacting an acylal of formula II

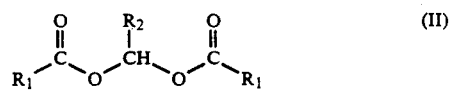

with thionyl chloride.

2. A process according to claim 1, wherein the acylal of formula II is reacted with at least an equimolar amount of thionyl chloride.

3. A process according to claim 1, wherein an excess of 1.1 times to twice the molar amount of thionyl chloride over the acylal of the formula II is used.

4. A process according to claim 1, wherein the reaction is carried out in a temperature range of from 40° C. to 120° C.

5. A process according to claim 1, wherein an excess of 1.1 times to twice the molar amount of thionyl chloride over the acylal of the formula II is used and the reaction is carried out in a temperature range of from 40° C. to 120° C.

6. A process according to claim 1, wherein separation of the reaction product by distillation is carried out under reduced pressure.

7. A process according to claim 1, wherein an acylal of formula II is heated to from 70° C. to 80° C., from 1.25 to 1.75 times the molar amount of thionyl chloride is added, the mixture is allowed to react for from 4 to 8 hours, and then the reaction product is separated by distillation under reduced pressure of from 10 mbar to 30 mbar.

8. A process according to claim 1, wherein there are prepared compounds of formula I wherein $R_1$ is $C_1$–$C_{14}$alkyl, $C_2$–$C_7$alkenyl, $C_3$–$C_7$alkynyl, or 3- to 8-membered cycloalkyl; or is phenyl or naphthyl each of which is unsubstituted or substituted by $C_1$–$C_4$alkyl, $C_1$–$C_4$alkoxy, halogen, trifluoromethyl and/or by nitro, or mono-, di- or tri-phenyl-$C_1$–$C_4$alkyl that is unsubstituted or substituted in the phenyl moiety by $C_1$–$C_4$alkyl, $C_1$–$C_4$alkoxy, halogen, trifluoromethyl and/or by nitro, and $R_2$ hydrogen is $C_1$–$C_7$alkyl or 3- to 8-membered cycloalkyl.

9. A process according to claim 5, wherein there are prepared compounds of formula I wherein $R_1$ is $C_1$–$C_1$-

4alkyl, $C_2$-$C_7$alkenyl, $C_3$-$C_7$alkynyl, or 3- to 8-membered cycloalkyl; or is phenyl or naphthyl each of which is unsubstituted or substituted by $C_1$-$C_4$alkyl, $C_1$-$C_4$alkoxy, halogen, trifluoromethyl and/or by nitro, or mono-, di- or tri-phenyl-$C_1$-$C_4$alkyl that is unsubstituted or substituted in the phenyl moiety by $C_1$-$C_4$alkyl, $C_1$-$C_4$alkoxy, halogen, trifluoromethyl and/or by nitro, and $R_2$ hydrogen is $C_1$-$C_7$alkyl or 3- to 8-membered cycloalkyl.

10. A process according to claim 1, wherein there are prepared compounds of formula I wherein $R_1$ is $C_1$-$C_7$alkyl and $R_2$ is hydrogen or $C_1$-$C_4$alkyl.

11. A process according to claim 1, wherein there are prepared compounds of formula I wherein $R_1$ is methyl, ethyl or secondary-linear or branched $C_3$-$C_7$alkyl, and $R_2$ is hydrogen or linear $C_1$-$C_4$alkyl.

12. A process according to claim 1, wherein there are prepared compounds of formula I wherein $R_1$ is methyl, ethyl or secondary-linear or branched $C_3$-$C_7$alkyl, and $R_2$ is hydrogen.

13. A process according to claim 1, wherein chloromethyl pivalate (of formula I; $R_1$=tert-butyl, $R_2$=hydrogen) is prepared.

14. A process according to claim 1, wherein chloromethyl pivalate (of formula I; $R_1$=tert-butyl, $R_2$=hydrogen) is prepared by heating methylene dipivalate to approximately 75° C., adding a 1.71-fold molar excess of thionyl chloride, stirring at 75° C. for 5 hours, and hydrolysing the resulting reaction mixture by the addition of water and separating the reaction mixture by distillation under reduced pressure of 20 mbar.

* * * * *